United States Patent [19]

Crouther et al.

[11] 4,215,700
[45] Aug. 5, 1980

[54] BLOOD COLLECTION DEVICE

[75] Inventors: Ronald Crouther, Manchester; Vincent H. Li, Maryland Heights, both of Mo.; Larry H. Dodge, LaHabra, Calif.

[73] Assignee: Sherwood Medical Industries Inc., St. Louis, Mo.

[21] Appl. No.: 937,013

[22] Filed: Aug. 25, 1978

[51] Int. Cl.³ .................. A61B 5/14; A61B 10/00
[52] U.S. Cl. ................................................ 128/763
[58] Field of Search ............... 128/763, 760, 762; 73/425.4 R; 215/355; 23/928, 931

[56] References Cited

U.S. PATENT DOCUMENTS

| 3,539,300 | 11/1970 | Stone | 23/253 |
| 3,545,932 | 12/1970 | Gilford | 23/253 |
| 3,607,098 | 9/1971 | Strande | 23/259 |
| 3,623,475 | 11/1971 | Sanz | 128/763 |
| 3,811,326 | 5/1974 | Sokol | 73/425.4 P |
| 3,902,477 | 9/1975 | Gerarde | 128/760 |
| 3,908,638 | 9/1975 | Porcher et al. | 128/763 |
| 3,926,521 | 12/1975 | Ginzel | 356/39 |
| 4,024,857 | 5/1977 | Blecher et al. | 128/763 |
| 4,050,451 | 9/1977 | Columbus | 128/764 |
| 4,132,225 | 1/1979 | Whattam | 128/763 |

FOREIGN PATENT DOCUMENTS 733440  7/1955  United Kingdom ............ 22/206

Primary Examiner—Willis Little
Attorney, Agent, or Firm—Stanley N. Garber; William R. O'Meara

[57] ABSTRACT

A blood collection device used in taking a small sample from a patient for test purposes is provided with a capillary tube and vented tube holder disposed in the upper end of a blood collection container. Integral radial extensions allow the container to be centrifuged in a centrifuge normally used for containers of larger diameter. An integral flexible strap connects a stopper to one of the radial extensions so that the stopper remains with the container.

5 Claims, 8 Drawing Figures

U.S. Patent  Aug. 5, 1980  Sheet 1 of 2  4,215,700
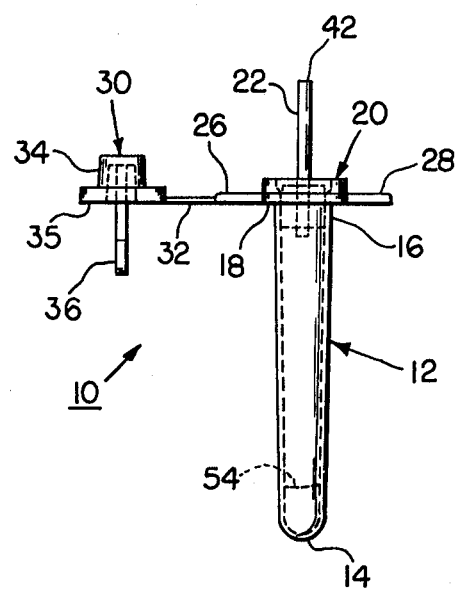
FIG. 1
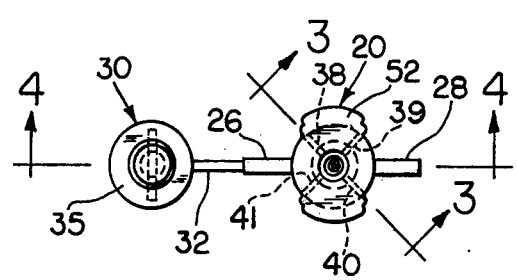
FIG. 2
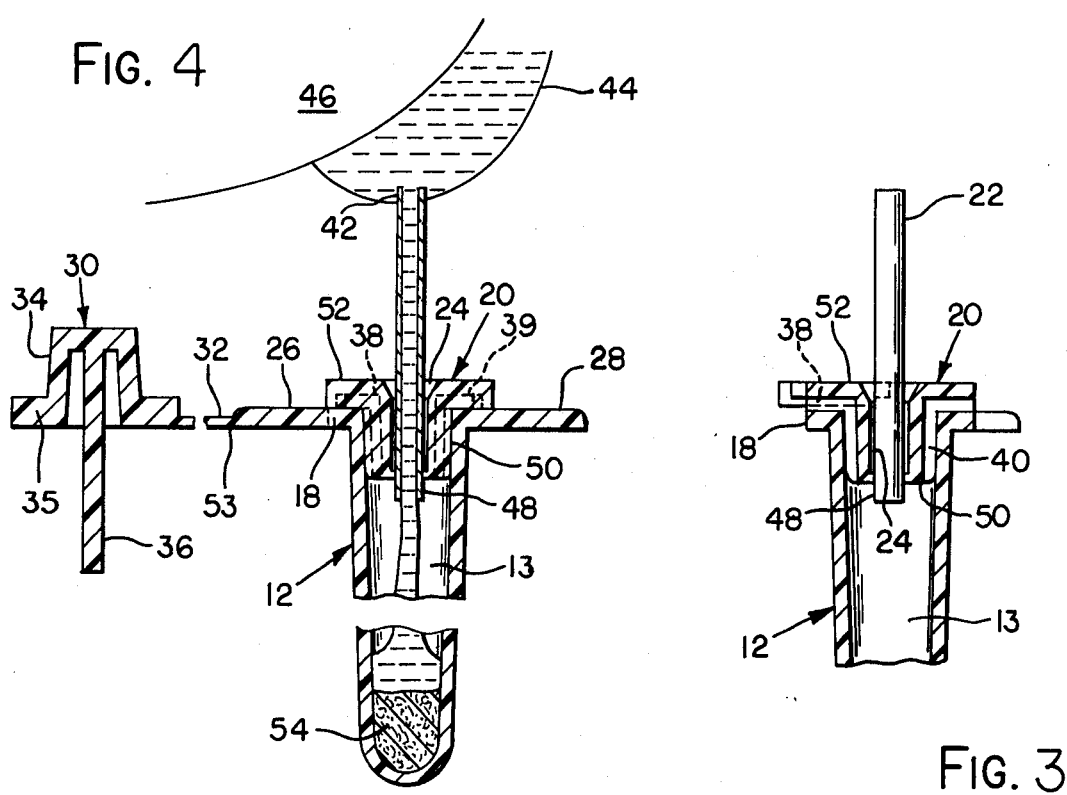
FIG. 4
FIG. 3

BLOOD COLLECTION DEVICE

BACKGROUND OF THE INVENTION

This invention relates to blood collection devices for use in testing the blood of a patient and more particularly to a blood collection device of the type employing a capillary tube through which blood enters a collection container.

Blood collection devices for collecting small blood samples for test purposes, such as percutaneous blood samples, often consist of a collection tube or container having a vented capillary tube holder supporting a capillary tube. Generally, an incision is made in a finger and the capillary tube used to convey blood from the finger to the container. After a sufficient amount of blood has been drawn, the holder and capillary tube are removed from the container and replaced by a stopper. The filled container is centrifuged to separate the lighter phase of the blood, plasma or serum, from the heavier cellular phase. The lighter phase is then removed from the container for test purposes.

There are certain disadvantages associated with conventional blood collection devices of the above type. For example, because such blood collection tubes are small and centrifuges are generally made for relatively larger collection tubes, special adapters have been used. The adapter allows the small collection tube to be supported in a relatively large opening in the tube support of the centrifuge. Such adapters, in general, add to the cost and complexity of the procedure. Also, generally the stoppers employed are made and stored separately, which further increases the cost.

SUMMARY OF THE INVENTION

It is therefore an object of the present invention to provide an improved blood collection device utilizing a capillary tube wherein the above undesirable features are substantially obviated.

Another object is to provide an improved blood collection device utilizing a capillary tube wherein the collection container can be placed in a centrifuge having a container supporting member with openings for collection containers of substantially greater size without requiring the use of an adapter, and wherein storage and handling of separated stoppers for collection containers is avoided.

In accordance with one aspect of the present invention, a blood collection device is provided which includes a plastic blood collection container, a capillary tube holder at one end of the container, a capillary tube connected to the holder and communicating with the interior of the container and having an end exterior thereof adapted for contact with a source of blood for conveying a blood sample to the container, extension means on the container so that it can be inserted into a container receiving opening of a centrifuge which has a diameter greater than that of the container without it falling through the opening, stopper means for closing one end of the container, and flexible strap means integrally connecting the stopper with the container.

BRIEF DESCRIPTION OF THE DRAWING

FIG. 1 is a side elevational view of a preferred embodiment of a blood collection device according to the present invention;

FIG. 2 is a top plan view of the device of FIG. 1;

FIG. 3 is an enlarged fragmentary, cross-sectional view taken along the line 3—3 of FIG. 2;

FIG. 4 is an enlarged cross-sectional view taken along the line 4—4 of FIG. 2 and illustrating the taking of a blood sample;

DESCRIPTION OF THE PREFERRED EMBODIMENT

Figure 7:
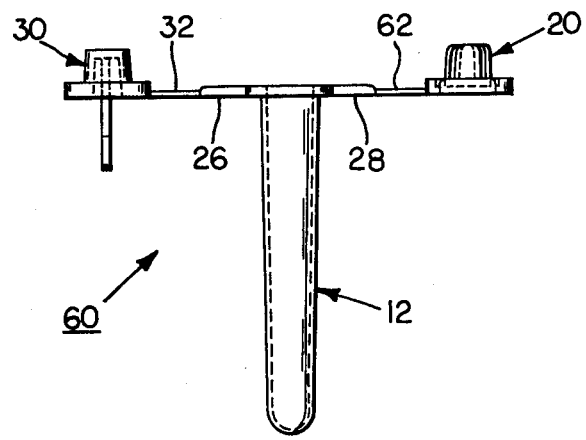
FIG. 7 illustrates one form of a molded structure from which the parts of the blood collection device of FIG. 1, except the capillary tube, are provided.

Referring now to the drawings, and particularly to FIGS. 1-3, there is shown a blood collection device indicated generally at 10 which is constructed in accordance with a preferred embodiment of the invention. Device 10 includes a blood collection container or tube 12 having an internal chamber 13, an integrally closed bottom end 14, and an upper open end 16 surrounded by an annular, radially extending integral flange or collar 18.

Disposed in the upper open end 16 of collection tube 12 is a capillary tube holder 20. Connected to holder 20 is a capillary tube 22 which is in fluid communication with the collection chamber 13 and provides a passage for the flow of blood into the collection tube, as will be discussed hereafter. As seen in FIGS. 3 and 4, capillary tube 22 is shown extending through a central throughbore 24 in holder 20. The bore 24 or a portion of the bore is sized to frictionally hold the inserted capillary tube 22 in a desired position. Preferably, the capillary tube 22 extends below and above the holder 20 as shown in the drawings.

Figure 6:
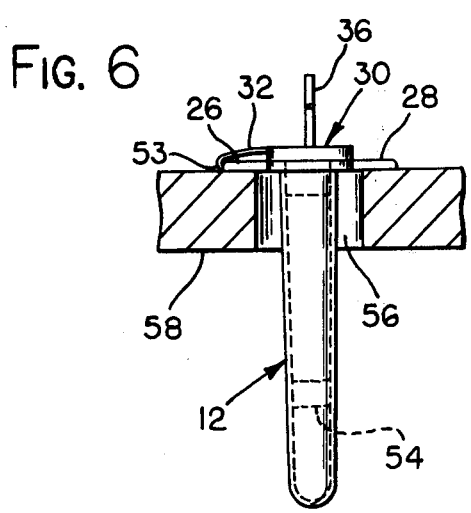
FIG. 6 illustrates the blood-filled collection device closed and inserted into an opening of a collection tube supporting member of a centrifuge.
Figure 5:
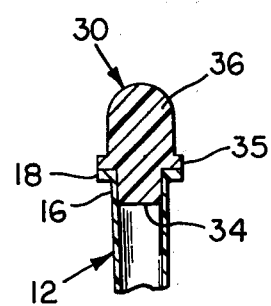
FIG. 5 is a fragmentary, cross-sectional view of the upper portion of the collection tube of FIG. 1, but with the stopper inserted in the upper end thereof.

The collection tube 12 is also provided with a pair of integral, diametrically disposed, rod-like supporting extensions or abutment members 26 and 28 that extend radially from the collar 18 for a purpose to be explained hereafter. A closure cap or stopper 30, shown in an inverted position in FIGS. 1-4, is integrally connected by a flexible connection or strap 32 to the outer end of extension 26. The stopper 30 has a plug portion 34 which is insertable into the open end 16 of the collection tube after the holder 20 and capillary tube 22 have been removed, as seen in FIGS. 5 and 6. The stopper 30 has an integral, enlarged annular top 35 of greater diameter than the open end of the collection tube and an axially extending, elongate handle or finger grip 36 to facilitate manual insertion and removal of the stopper into and out of the collection tube 12.

As seen in FIGS. 2 and 3, holder 20 is provided with four similar vent passages 38, 39, 40 and 41, for the venting of the collection chamber 13 to atmosphere so that air can escape from the chamber when blood flows into the chamber during the taking of a blood sample, as indicated in FIG. 4.

In taking a blood sample, the distal or upper end, indicated at 42, of capillary tube 22 is disposed within a source of blood 44, illustrated in FIG. 4 as a globule of blood, for example, such as formed by an incision into a finger 46 of a patient. Blood 44 flows through the capillary tube 22 and into collection tube 12 by gravity and capillary effects. The inner or bottom end, indicated at 48, of tube 22, is shown extending into chamber 13 below the bottom end of holder 20. As blood 44 flows into the collection tube 12 it displaces air which escapes from chamber 13 by flowing through the vent passages 38–41 to the atmosphere.

As best seen in FIGS. 3 and 4, holder 20 includes an annular plug portion 50 which frictionally fits within the upper end of the collection tube 12. Integrally connected to the plug 50 is an upper plate or top 52 which extends radially outwardly beyond the tube collar 18 and engages the top of the collar when the holder 20 is inserted into collection tube 12. The top 52 is grasped for manual insertion and removal of the holder 20 from the collection tube 12.

The vent passages 38–41, as best seen in FIGS. 2–4, are in the form of sidewall grooves extending from the bottom end of plug portion 50 within chamber 13 to the peripheral sidewall of the holder 20. Each vent passage has a substantially vertical portion in plug portion 50 which connects with a horizontal or radially extending portion in the bottom wall of the top 52. The four vent passages are circumferentially spaced about the holder as best seen in FIG. 2. The upper wall of top 52 extends over the vent passages and, since the radially outer end of each vent passage is in the peripheral sidewall of top 52, there is little chance of any blood that might flow down the outside of the capillary tube flowing into any of the vent passages 38–41. However, even if one or some of the vent passages were to become clogged under unusual conditions, one open vent passage would be sufficient for the escape of air from the collection chamber 13 to the atmosphere to allow blood to enter the chamber.

After the desired amount of blood 44 has flowed into the collection chamber 13, the holder 20 and capillary tube 22 are removed from the collection tube 12 and discarded. The integrally connected stopper 30 is then inverted, while connected by the flexible strap 32 to the radial extension 26, and inserted into the open end 16 of the filled collection tube 12, as illustrated in FIGS. 5 and 6. The plug portion 34 is moved into the collection tube until the top 35 engages the top of collar 18 or upper end of tube 12, the stopper sealingly closing the open end 16 of the collection tube. Conventionally, the closed collection tube 12 containing the sample of blood is subsequently placed in a centrifuge to separate the lighter phase, serum or plasma, from the heavier cellular phase for the purpose of clinically testing the lighter phase.

When the stopper 30 is manually inverted and inserted into the collection tube 12, the strap bends at or near the junction of the strap and extension 26, indicated at 53 in FIGS. 4 and 6, since the extension is thicker and therefore more rigid than strap 32. The strap is dimensioned such that, as stopper 30 is pivoted about the outer end of the extension or junction 53, it is in position to enter the open end 16 of the collection tube. With this construction, the stopper 30 tends to be automatically directed toward and into the upper end 16 of the collection tube by strap 32 when manually pivoted about the junction 53 to thereby facilitate the closure of the blood-filled tube.

Preferably, a suitable quantity of gel-like material 54, as shown in FIGS. 1, 4 and 6, is disposed in the bottom of collection chamber 13 and serves as a blood phase partitioning material. Gel 54 may be of the polybutene-silica powder type described in U.S. Ser. No. 642,514 filed 12-16-75, which is assigned to the same assignee as this application, or of the silicone-silica powder type described in U.S. Pat. No. 3,852,194. Gel 54 is preferably a thixotropic material inert to blood, having a specific gravity intermediate the specific gravities of the separated lighter and heavier blood phases, that is, between about 1.02 and 1.09, and is flowable under predetermined centrifugal forces. Thus, during centrifugation of the blood-filled collection tube 20, the gel 54 automatically flows to the interface of the separated phases to serve as a liquid impervious barrier between the phases after centrifugation.

In FIG. 6, the closed, sample-filled collection tube 12 is shown disposed in an opening 56 of a tube supporting member or arm 58 of a centrifuge. The opening 56 is conventionally made large enough to accommodate blood collection tubes of various sizes including tubes of a size larger than that of tube 12. Because the collection tube 12 is provided with the radial extensions 26 and 28, which abut the top of arm 58, the collection tube 12, even though it has a relatively small outer diameter, cannot fall through the opening 56 in the centrifuge since the collection tube is supported by the extensions 26 and 28. Thus, the relatively small tube 12 can be centrifuged in conventional centrifuges or where the centrifuge supporting arm opening is sized to normally support tubes of greater average diameter than that of the collection tube 12, and without the need of a special adapter.

Figure 8:
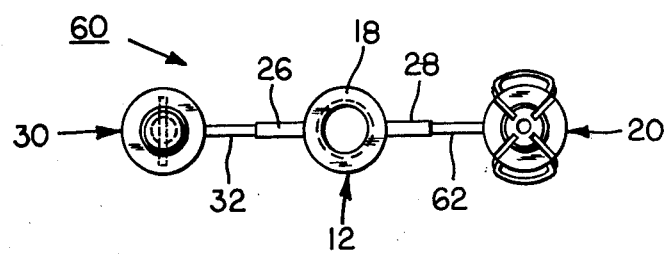
FIG. 8 is a top plan view of the molded structure of FIG. 7.

As is apparent from the drawings and especially from FIG. 8, the distance between the radially outer ends of extensions 26 and 28 in the illustrated embodiment is more than twice the outer diameter of collar 18, the part of tube 12 having the maximum diameter, so the collection tube 12 can be satisfactorily used even where there is a substantial difference in size between the maximum diameter of the collection tube and centrifuge arm opening 56. Since the width or circumferential dimension of each of the extensions 26 and 28 is relatively small, about or less than one-third of its radial length, considerable savings in plastic material is obtained. Also, collection tubes with such extensions can be used in centrifuges where the tube supporting arm contains a plurality of relatively small and closely placed collection tube receiving openings since the collection tubes can be positioned so that the radial extensions are in a staggered arrangement. That is, so that a relatively large number of collection tubes can be economically centrifuged together in a supporting arm of relatively limited size or area.

The gel 54 in FIG. 6 is shown in its final position after the filled collection tube 12 has been centrifuged and the light and heavy blood phases separated. The light phase will be above the gel 54 and the heavier cellular phase below the gel with the gel serving as a liquid impervious barrier or partition between the two phases. The tube 12 may then be removed from centrifuge and transported to a blood testing station where the stopper 30 is removed and the light phase of the blood poured or otherwise removed from the collection tube for clinical testing.

FIGS. 7 and 8 illustrate a unitary molded structure 60 providing the parts of collection device 10 of FIG. 1, except the capillary tube 22. The capillary tube 22, while illustrated as a separate glass tube connected to the holder, may in some cases be made of a suitable plastic. When made of plastic, the capillary tube may be made separately or as an integral part of holder 20. The holder may be molded as a separate part if desired or the entire device 10 may be economically made from a single mold with the tube 22 integrally connected to the holder 20.

The single-piece structure 60 is shown with a flexible strap 62 between the radial extension 28 and the holder 20, and could be used to retain the holder with the collection tube 12. Strap 62 permits the holder to be placed in the open end of the collection tube for taking a blood sample. Thereafter, the strap 62 and holder 20 may be disconnected from tube 12 and the tube closed by stopper 30 and centrifuged. Preferably, the holder 20 is disconnected and inserted into the collection tube during manufacture of the device 10, such as in the embodiment of FIG. 1. In this way, after a blood sample has been taken, the holder 20 and tube 22 can be readily removed from the collection tube 12 and discarded. Where holder 20 is to be separated before use, the mold from which the device is made is preferably constructed so that the molded structure as it comes from the mold is substantially free of the strap 62, that is, with the holder 20 close to the outer end of extension 28. Also, the top 52 of the holder may be molded so that it has a circular outer periphery rather than the generally oblong shape as seen in FIG. 2.

The device 10 may be made of a suitable thermoplastic, for example, polypropylene, polyethylene, polyvinylchloride, or the like, and preferably of transparent plastic. The collection and capillary tubes may be coated with an anti-coagulant such as heparin where plasma rather than serum is to be used.

As various changes could be made in the above construction without departing from the scope of the invention, it is intended that all matter contained in the above description or shown in the accompanying drawings shall be interpreted as illustrative and not in a limiting sense.

What is claimed is:

1. A blood collection device comprising a plastic container having a blood collection chamber closed at the bottom end and open at the upper end, a capillary tube holder removably connectable to the upper open end of the container, capillary tube means connected to said holder with one end in fluid communication with said chamber and the opposite end externally of said chamber and adapted to be disposed in contact with a source of blood for conveying blood from the source to said chamber when in use, a pair of circumferentially spaced, generally radially outwardly extending plastic extension members integrally connected to the upper portion of said container with the radially outer ends thereof at different circumferential locations about said container and with said outer ends spaced apart a distance at least twice that of the diameter of the upper end of said container for supporting said container when inserted into a container receiving opening of a centrifuge which has a diameter greater than the maximum outer diameter of said container each of said extension members having a circumferential width less than its radial length and less than the diameter of the upper end of said container stopper movable into and out of a position sealably closing the upper end of said container, and flexible strap means integrally connecting said stopper to said container for allowing said stopper to be moved into and out of said sealably closing position while being integrally connected to said container.

2. The device of claim 1 wherein said strap is integrally connected between said stopper and the outer end of one of said extension members.

3. The device of claim 2 wherein said extension members are relatively narrow substantially diametrically oppositely disposed rods extending substantially in opposite directions from said container.

4. The device of claim 1, 2, or 3 wherein the circumferential width of each of said extension members is about or less than one-third of the radial length thereof.

5. A blood collection device comprising a plastic container having a blood collection chamber closed at the bottom end and open at the upper end, a capillary tube holder removably connectable to the upper open end of the container, capillary tube means connected to said holder with one end in fluid communication with said chamber and the opposite end externally of said chamber and adapted to be disposed in contact with a source of blood for conveying blood from the source to said chamber when in use, means for venting said chamber, a pair of generally radially outwardly extending plastic extension members integrally connected to the upper portion of said container with the radially outer ends thereof at different circumferential locations about said container for supporting said container when inserted into a container receiving opening of a centrifuge which has a diameter greater than the maximum outer diameter of said container, each of said extension members having a circumferential width about or less than one-third of the radial length thereof, a stopper movable into and out of a position sealably closing the upper end of said container, and flexible strap means integrally connecting said stopper to said container for allowing said stopper to be moved into and out of said sealably closing position while being integrally connected to said container.

* * * * *